United States Patent
Kuroda

(10) Patent No.: US 7,803,626 B2
(45) Date of Patent: Sep. 28, 2010

(54) AUTOMATIC ANALYZER AND METHOD FOR DETERMINING ABNORMALITY IN DISPENSING OF DISPENSING SYSTEM

(75) Inventor: Akihisa Kuroda, Mishima (JP)

(73) Assignee: Beckman Coulter, Inc., Brea, CA (US)

( * ) Notice: Subject to any disclaimer, the term of this patent is extended or adjusted under 35 U.S.C. 154(b) by 78 days.

(21) Appl. No.: 12/324,112

(22) Filed: Nov. 26, 2008

(65) Prior Publication Data

US 2009/0133512 A1    May 28, 2009

Related U.S. Application Data

(63) Continuation of application No. PCT/JP2007/060644, filed on May 24, 2007.

(30) Foreign Application Priority Data

May 26, 2006  (JP) .............................. 2006-147311

(51) Int. Cl.
    *G01N 35/10* (2006.01)
(52) U.S. Cl. ..................... 436/49; 73/1.74; 73/864.22; 422/81
(58) Field of Classification Search ............... 73/1.74, 73/864.22; 134/18, 113; 422/81; 436/49
    See application file for complete search history.

(56) References Cited

U.S. PATENT DOCUMENTS

| 4,180,085 | A | * | 12/1979 | Berges et al. | 134/57 D |
| 7,704,457 | B2 | * | 4/2010 | Patton | 422/81 X |
| 2009/0114255 | A1 | * | 5/2009 | Kato | 134/56 R |
| 2009/0254309 | A1 | * | 10/2009 | Kubota et al. | 702/185 |

FOREIGN PATENT DOCUMENTS

| JP | 05-223830 | | 9/1993 |
| JP | 2001029689 | A * | 2/2001 |
| JP | 2002-122604 | | 4/2002 |
| JP | 2004-271266 | | 9/2004 |
| JP | 3119773 | U | 3/2006 |

* cited by examiner

*Primary Examiner*—Thomas P Noland
(74) *Attorney, Agent, or Firm*—Townsend and Townsend and Crew, LLP

(57) ABSTRACT

An automatic analyzer is for analyzing a reaction liquid in which a specimen and a reagent have been reacted. The automatic analyzer includes a dispensing system, a detector, and a determiner. The dispensing system includes a dispensing nozzle by which the specimen and the reagent are dispensed; and a dispensing pipe connected to the dispensing nozzle and filled with a cleaning liquid. The dispensing nozzle is cleaned with the cleaning liquid discharged from the dispensing nozzle. The detector detects a discharge amount of the cleaning liquid discharged from the dispensing nozzle. The determiner determines whether the detected discharge amount of the cleaning liquid is over a predetermined value which is less than a pre-set discharge amount of the cleaning liquid. The determiner determines that the dispensing is abnormal if the detected discharge amount is equal to or less than the predetermined value.

6 Claims, 7 Drawing Sheets

AUTOMATIC ANALYZER AND METHOD FOR DETERMINING ABNORMALITY IN DISPENSING OF DISPENSING SYSTEM

CROSS-REFERENCE TO RELATED APPLICATIONS

This application is a continuation of PCT international application Ser. No. PCT/JP2007/060644 filed on May 24, 2007 which designates the United States, incorporated herein by reference, and which claims the benefit of priority from Japanese Patent Application No. 2006-147311, filed on May 26, 2006, incorporated herein by reference.

BACKGROUND OF THE INVENTION

1. Field of the Invention

The present invention relates to an automatic analyzer and a method for determining an abnormality in dispensing of a dispensing system.

2. Description of the Related Art

Conventionally, in an automatic analyzer which analyzes a biological sample such as blood and bodily fluid, a liquid sample such as a specimen and a reagent is dispensed by a dispensing system, and the specimen and the reagent are dispensed by a dispensing nozzle connected with a dispensing pipe filled with cleaning liquid (see Japanese Patent Application Laid-Open No. 2004-271266, for example). In the dispensing system which dispenses the biological sample, an abnormality in dispensing occurs over time because a foreign substance and a taint caused by the biological sample adhere to components such as the dispensing nozzle and the dispensing pipe, or because the cleaning liquid is leaked from a pipe, a syringe pump or from the like, or because a driving unit which drives the syringe pump and the like has an operational failure.

Thus, the automatic analyzer regularly carries out maintenance and replaces components of the dispensing system, or checks accuracy management data obtained by measuring an accuracy-management specimen for management of dispense accuracy. Specifically, the measurement of the accuracy-management specimen is useful for detecting an abnormality in dispensing, and the abnormality in dispensing can be immediately detected as a number of measurements increases. Thus, the more the number of measurements of the accuracy-management specimen increases, the higher a probability of detecting an abnormality in a measured value of the specimen caused by the abnormality in dispensing becomes.

SUMMARY OF THE INVENTION

An automatic analyzer according to an aspect of the present invention is for analyzing a reaction liquid in which a specimen and a reagent have been reacted. The automatic analyzer includes a dispensing system, a detector, and a determiner. The dispensing system includes a dispensing nozzle by which the specimen and the reagent are dispensed; and a dispensing pipe connected to the dispensing nozzle and filled with a cleaning liquid. The dispensing nozzle is cleaned with the cleaning liquid discharged from the dispensing nozzle. The detector detects a discharge amount of the cleaning liquid discharged from the dispensing nozzle. The determiner determines whether the detected discharge amount of the cleaning liquid is over a predetermined value which is less than a pre-set discharge amount of the cleaning liquid. The determiner determines that the dispensing is abnormal if the detected discharge amount is equal to or less than the predetermined value.

A method according to another aspect of the present invention is for determining an abnormality in dispensing of a dispensing system in which a specimen and a reagent are dispensed by a dispensing nozzle connected to a dispensing pipe filled with a cleaning liquid, and the dispensing nozzle is cleaned with the cleaning liquid discharged from the dispensing nozzle. The method includes detecting a discharge amount of the cleaning liquid discharged from the dispensing nozzle; and determining whether the detected discharge amount of the cleaning liquid is over a predetermined value that is less than a pre-set discharge amount of the cleaning liquid, and determining that the dispensing is abnormal if the detected discharge amount is equal to or less than the predetermined value.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
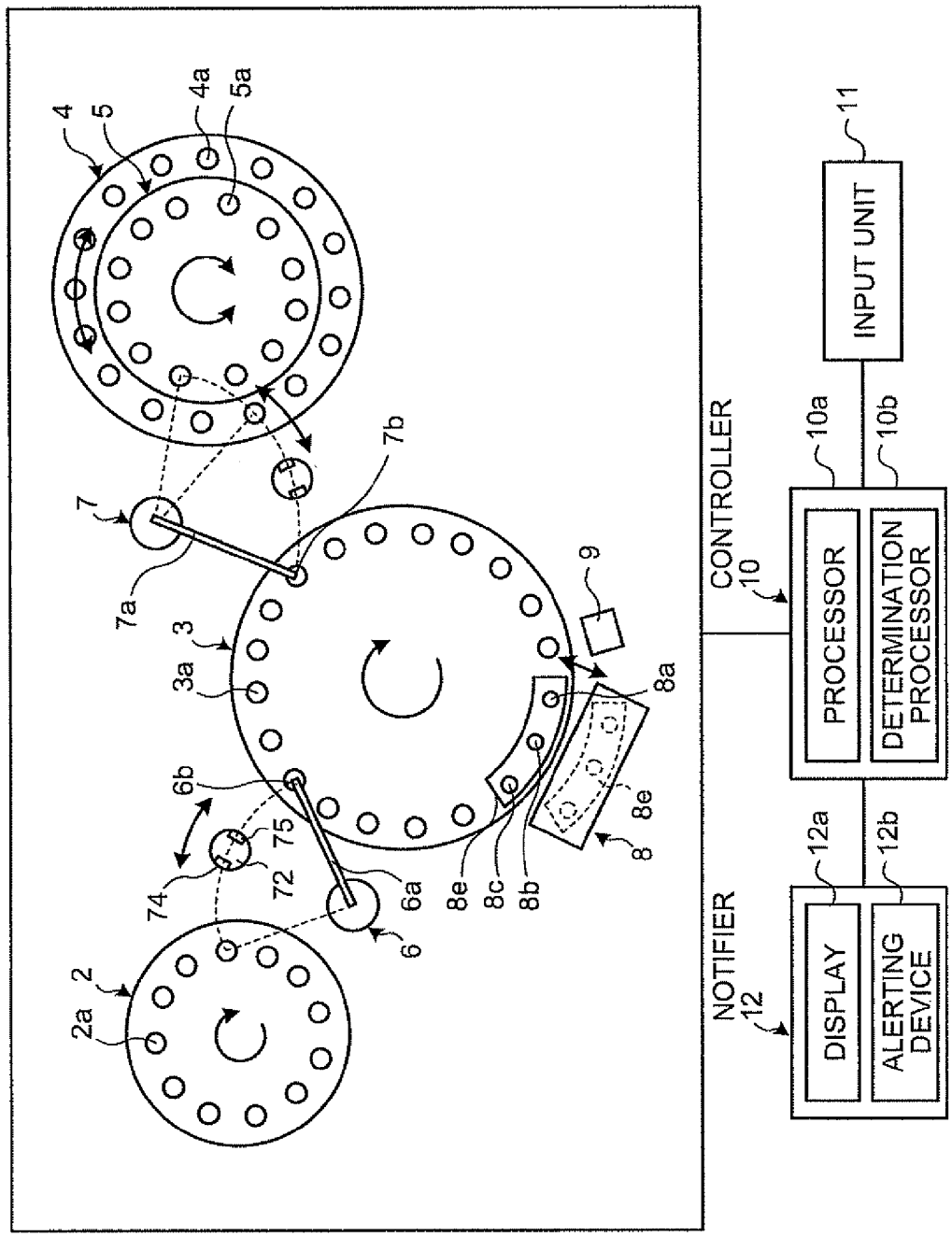
FIG. 1 is a schematic configuration diagram of an automatic analyzer, having a dispensing system, according to a first embodiment of the present invention.
Figure 2:
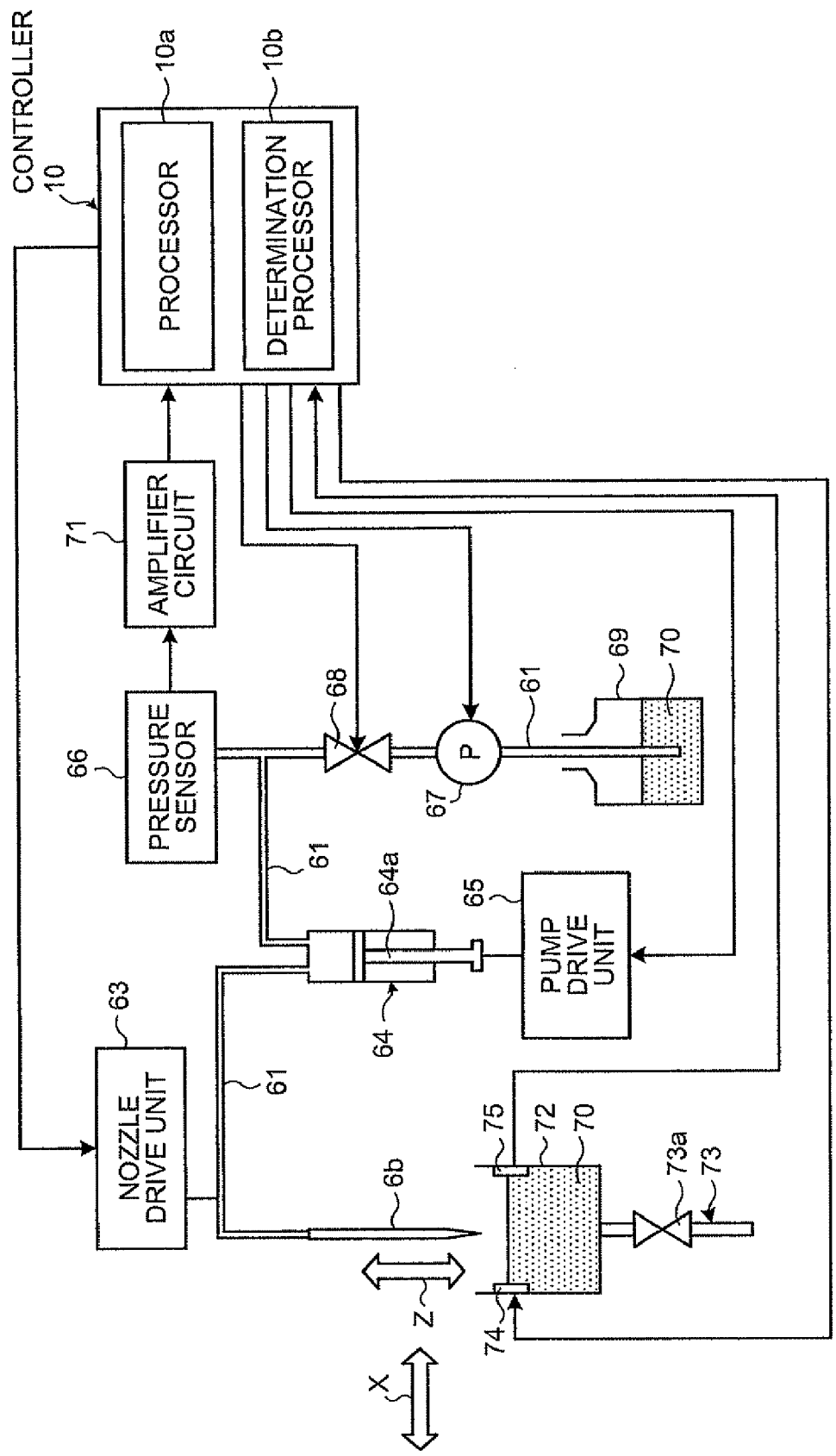
FIG. 2 is a block diagram of a configuration of the dispensing system of the automatic analyzer of FIG. 1.

An automatic analyzer and a method for determining an abnormality in dispensing of a dispensing system according to a first embodiment of the present invention are described in detail below with reference to the drawings. FIG. 1 is a schematic configuration diagram of the automatic analyzer having the dispensing system. FIG. 2 is a block diagram of a configuration of the dispensing system of the automatic analyzer of FIG. 1.

As shown in FIGS. 1 and 2, the automatic analyzer 1 includes a specimen table 2, a reaction table 3, a first reagent table 4, a second reagent table 5, a specimen dispensing system 6, a reagent dispensing system 7, a cleaning system 8, a photometry unit 9, and a controller 10.

As shown in FIG. 1, the specimen table 2 has plural specimen vessels 2a containing a specimen arranged thereon at same intervals in a circle, and rotates intermittently in a right direction along the arrow to transport the specimen vessels 2a in the direction along the circle.

As shown in FIG. 1, the reaction table 3 has plural reaction vessels 3a arranged thereon at the same intervals in a circle, and rotates intermittently in a right direction along the arrow to transport the reaction vessels 3a around a circle. For example, the reaction vessel 3a is made of a transparent material, for example, glass including a heat-resistant glass, and a synthetic resin such as cyclic olefin and polystyrene.

As shown in FIG. 1, the first reagent table 4 has plural first reagent vessels 4a containing the first reagent arranged thereon at same intervals in a circle, and rotates in left-right directions along the arrow to transport the first reagent vessel 4a around a circle. The second reagent table 5 has plural second reagent vessels 5a containing the second reagent arranged thereon at same intervals in a circle, and rotates in left-right directions to transport the second reagent vessels 5a around a circle. The first reagent table 4 and the second reagent table 5 are rotated with a same center, independently of each other.

The specimen dispensing system 6 is a dispensing system that dispenses the specimen contained in the specimen vessel 2a into the reaction vessel 3a, and is arranged between the specimen table 2 and the reaction table 3 as shown in FIG. 1. The reagent dispensing system 7 configured similarly to the specimen dispensing system 6 is a dispensing system that dispenses the reagent contained in the first reagent vessel 4a or the second reagent vessel 5a into the reaction vessel 3a, and is arranged between the reaction table 3 and the first reagent table 4 as shown in FIG. 1. The specimen dispensing system 6 and the reagent dispensing system 7 have dispensing nozzles 6b, 7b which dispense the reagent into arms 5a, 7a which rotate in directions along the arrows on a horizontal plane, respectively.

The specimen dispensing system 6 and the reagent dispensing system 7 are configured in a similar manner, and the specimen dispensing system 6 is described below.

The specimen dispensing system 6 includes, in addition to the dispensing nozzle 6b, a dispensing pump 64, a pressure sensor 66, a cleaning-water pump 67, an amplifier circuit 71, and a cleaning tank 72 as shown in FIG. 2. The specimen dispensing system 6 is used under control by the controller 10, and can be also used independently in a manner shown in FIG. 2.

The dispensing nozzle 6b is connected to the dispense pump 64, the pressure sensor 66, and the cleaning-water pump 67 via a pipe 61. The dispensing nozzle 6b is moved by a nozzle drive unit 63 in horizontal directions along the arrow X or in vertical directions along the arrow Z in FIG. 2, sucks in the specimen from the specimen vessels 2a sequentially transported by the specimen table 2 to a place below the dispensing nozzle 6b, and dispenses the specimen by discharging the specimen into the reaction vessels 3a.

The dispense pump 64 is a syringe pump which makes the dispensing nozzle 6b suck in the specimen in the specimen vessel 2a and makes the dispensing nozzle 6b discharge the specimen from the specimen vessel 2a into the reaction vessel 3a transported by the reaction table 3; a piston 64a is reciprocated by a pump drive unit 65. The dispensing pump 64 is driven by the pump drive unit 65 based on a discharge amount of cleaning water and a dispensing amount previously input from the input unit 11 to the controller 10. When the discharge amount of cleaning water and the dispensing amount are constant, the amount of reciprocation of the piston 64a becomes constant as well.

The pressure sensor 66 detects pressure inside the pipe 61 and outputs the pressure to the amplifier circuit 71 as a pressure signal (analog).

The cleaning-water pump 67 sucks up deaerated cleaning water 70 stored in a tank 69, and pressurizes and transports the cleaning water 70 into the pipe 61 via an electromagnetic valve 68 arranged between the cleaning water-pump 67 and the pressure sensor 66. In the description above, the electromagnetic valve 68 is switched to "OPEN" by a control signal from the controller 10 when the sucked cleaning water 70 is pressurized and transported into the pipe 61 whereas the electromagnetic valve 68 is switched to "CLOSE" when the dispensing nozzle 6b sucks in the specimen from the specimen vessel 2a via the dispensing pump 64, and discharges the specimen into the reaction vessel 3a.

The amplifier circuit 71 amplifies the pressure signal (analog) output from the pressure sensor 66, and outputs the amplified pressure signal to the controller 10.

As shown in FIGS. 1 and 2, the cleaning tank 72 is arranged right under the dispensing nozzle 6b that is arranged between the specimen table 2 and the reaction table 3. The cleaning tank 72 cleans the dispensing nozzle 6b that has dispensed the specimen with the stored cleaning water 70. A discharge pipe 73 with a valve 73a is connected to a lower part of the cleaning tank 72. After an inner wall of the dispensing nozzle 6b that has dispensed the specimen is cleaned as the cleaning water 70 is discharged into the cleaning tank 72 by the dispense pump 64, the dispensing nozzle 6b is moved down by the nozzle drive unit 63 and inserted into the cleaning water 70 to clean an outer wall thereof in the cleaning tank 72. In the description above, the dispensing nozzle 6b is inserted into the cleaning water 70 farther than when inserted into the specimen to perform dispensing. The cleaning tank 72 opens the valve 73a and discharges the cleaning water 70 through the discharge pipe 73 after the cleaning of the dispensing nozzle 6b. Further, the cleaning tank 72 includes sensors 74, 75, which detect the discharge amount of the cleaning water 70 discharged by the dispensing nozzle 6b, attached to an inner wall thereof.

The sensors 74, 75 are realized by a transmissive light sensor for example, and arranged at opposing positions in an inner surface of the cleaning tank 72, the opposing positions corresponding to a liquid-surface position of the discharged cleaning water 70. The sensor 74 emits measurement light to the sensor 75. Then, the sensor 75 receives the measurement light emitted by the sensor 74, and outputs to the controller 10 a light signal corresponding to an amount of light received. The controller 10 acquires the discharge amount of the cleaning water 70 discharged by the dispensing nozzle 6b based on the light signal emitted by the sensor 74 and on the light signal of the measurement light received by the sensor 75, and stores therein the discharge amount as a discharge-amount signal.

Figure 3:
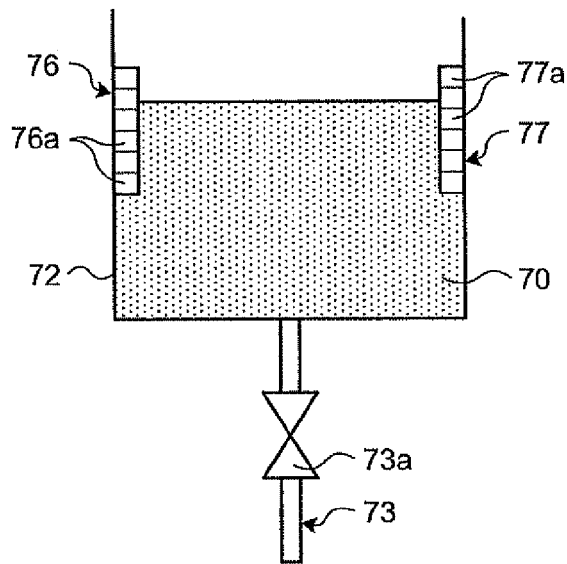
FIG. 3 is an enlarged view of a cleaning tank showing one process of acquiring a discharge amount of cleaning water.

Further, as shown in FIG. 3, the discharge amount of the cleaning water 70 may be acquired in such a manner that the sensor 74 is used in place of a light-emitting-device array 76 consisting of plural minute light-emitting devices 76a which are arranged in line in a vertical direction, and the sensor 75 is used in place of a light-receiving-device array 77 consisting of plural minute light-receiving devices 77a which are arranged in line in the vertical direction. In this case, the light-emitting-device array 76 and the light-receiving-device array 77 are arranged at opposing positions on an inner-wall surface of the cleaning tank 72. Further, the discharge amount of the cleaning water 70 may be acquired from a vertical position of the light-receiving devices 77a receiving light which is emitted by each light-emitting device 76a corresponding to the discharge amount of the cleaning water 70 discharged into the cleaning tank 72.

The cleaning system 8 cleans the reaction vessel 3a after the measurement finishes, and includes a suction nozzle 8a, a discharge nozzle 8b, and a suction nozzle 8c for the cleaning water, and a driving mechanism Se, which moves the nozzles 8a to 8c up and down as a single unit and reciprocates the nozzles between the reaction table 3 and the cleaning system 8.

The photometry unit 9 optically measures reaction liquid where the specimen and the reagent which are dispensed into the reaction vessel 3a by the specimen dispensing system 6 and the reagent dispensing system 7, respectively, have been reacted, and outputs the measurement result to the controller 10.

The controller 10, which is realized by a micro computer or the like for example, controls an operation of each unit of the automatic analyzer 1, and analyzes components, concentration, and the like of the specimen based on the measurement result of the photometry unit 9. As shown in FIGS. 1 and 2, the controller 10 includes a processor 10a and a determination processor lob. The processor 10a, which is realized by an A/D converter for example, is a unit which performs a process to convert the pressure signal (analog) of the pressure sensor 66 in the specimen dispensing system 6 and the reagent dispensing system 7 into a digital signal. The determination processor 10b determines whether there is an abnormality in dispensing based on the discharge amount of the cleaning water 70 detected by the sensors 74, 75 attached to the cleaning tank 72. The determination processor 10b stores therein a pre-set discharge amount of the cleaning water 70. The determination processor 10b determines whether a detected discharge amount of the cleaning water 70 detected by the sensors 74, 75 is over a predetermined value which is less than the pre-set discharge amount of the cleaning water 70, and determines that the dispensing is abnormal when the discharge amount is less than or equal to the predetermined value, in other words, is 90% or less of the pre-set discharge amount. Further, as shown in FIG. 1, the controller 10 is connected with the input unit 11 such as a keyboard, and with a notifier 12. The notifier 12 includes a display 12a to display a notification of an operational status of the automatic analyzer 1 and the abnormality in dispensing, and an alerting device 12b to notify that there is the abnormality in dispensing by an alert.

In the automatic analyzer 1 configured as above, the specimens in each specimen vessel 2a which is stored in the specimen table 2 by the specimen dispensing system 6 are sequentially dispensed into the plural reaction vessels 3a which are transported along a circular direction by the rotating reaction table 3. A reagent in the first reagent vessel 4a or a reagent in the second reagent vessel 5a or both are sequentially dispensed by the specimen dispensing system 7 into the reaction vessel 3a into which the specimen has been dispensed. Further, the reagent and the specimen are reacted while the reaction vessel 3a into which the reagent and the specimen are dispensed is transported by the reaction table. When the reaction vessel 3a passes the photometry unit 9, reaction liquid inside the reaction vessel 3a is optically measured, and components, concentration, and the like are analyzed by the controller 10. Further, after the analysis finishes, the reaction vessel 3a is cleaned by the cleaning system 8 and reused for the analysis of the specimen.

Figure 4:
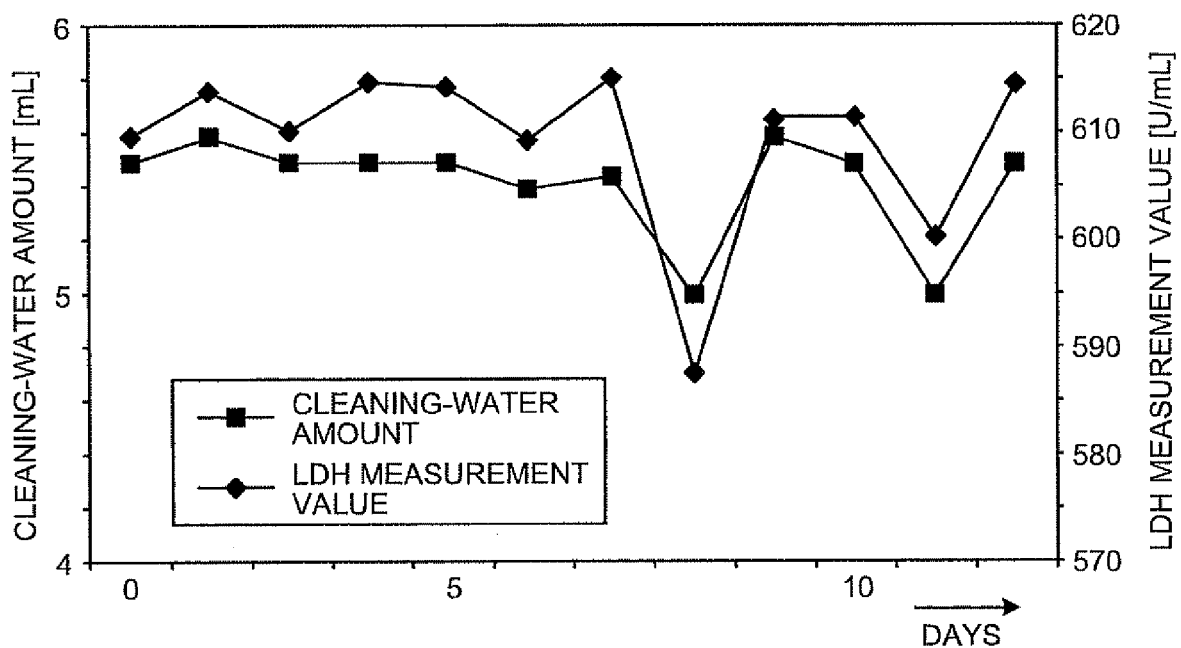
FIG. 4 is a diagram of a relation between the discharge amount of the cleaning water from a dispensing nozzle measured once a day and a measurement value of a lactate dehydrogenase being an analysis item of an accuracy-management specimen in the automatic analyzer.

In the description above, the automatic analyzer 1 checks out a relation between the contamination or an adhesion of foreign substances to the dispensing nozzle 6b, which is caused over time by the analysis of the specimen, and accuracy-management data acquired by measuring the accuracy-management specimen. FIG. 4 shows a relation between a discharge amount (mL) of the cleaning water from the dispensing nozzle 6b that is measured once a day and a measurement value (U/mL) of a lactate dehydrogenase (LDH) being an analysis item of the accuracy-management specimen in the automatic analyzer 1.

As can be seen by a result in FIG. 4, the discharge amount of the cleaning water drastically decreases at the eighth day and the eleventh day, and along with the decrease, the measurement value of LDH also drastically decreases. Contamination and the like are removed as the dispensing nozzle 6b is cleaned with detergent before the analysis on the ninth day and the twelfth day, and then the discharge amount of the cleaning water and the measurement value of LDH returns to the former condition as shown in FIG. 4. Further, from the seventh day to the eighth day, and from the tenth day to eleventh day, while the discharge amount of the cleaning water decreases by 8.3 to 9.1%, the measurement value of LDH decreases by 1.8 to 4.4%.

As described, when the contamination and the like are adhered to the dispensing nozzle 6b, the dispensing amount of the accuracy-management specimen and the discharge amount of the cleaning water discharged from the dispensing nozzle 6b decrease, and the measurement value of LDH decreases. In this case, changes in the discharge amount of the cleaning water are found out to be larger than changes in the measurement value of LDH. Thus, the automatic analyzer 1 can determine whether there is the abnormality in dispensing based on the discharge amount of the cleaning water discharged from the dispensing nozzle 6b, without actually carrying out an analysis using the accuracy-management specimen and the reagent. The present invention is made based on this observation, and can allow quick, easy determination of the abnormality in dispensing prior to the measurement of the specimen, thereby avoiding wasting cost and time for the measurement.

Figure 5:
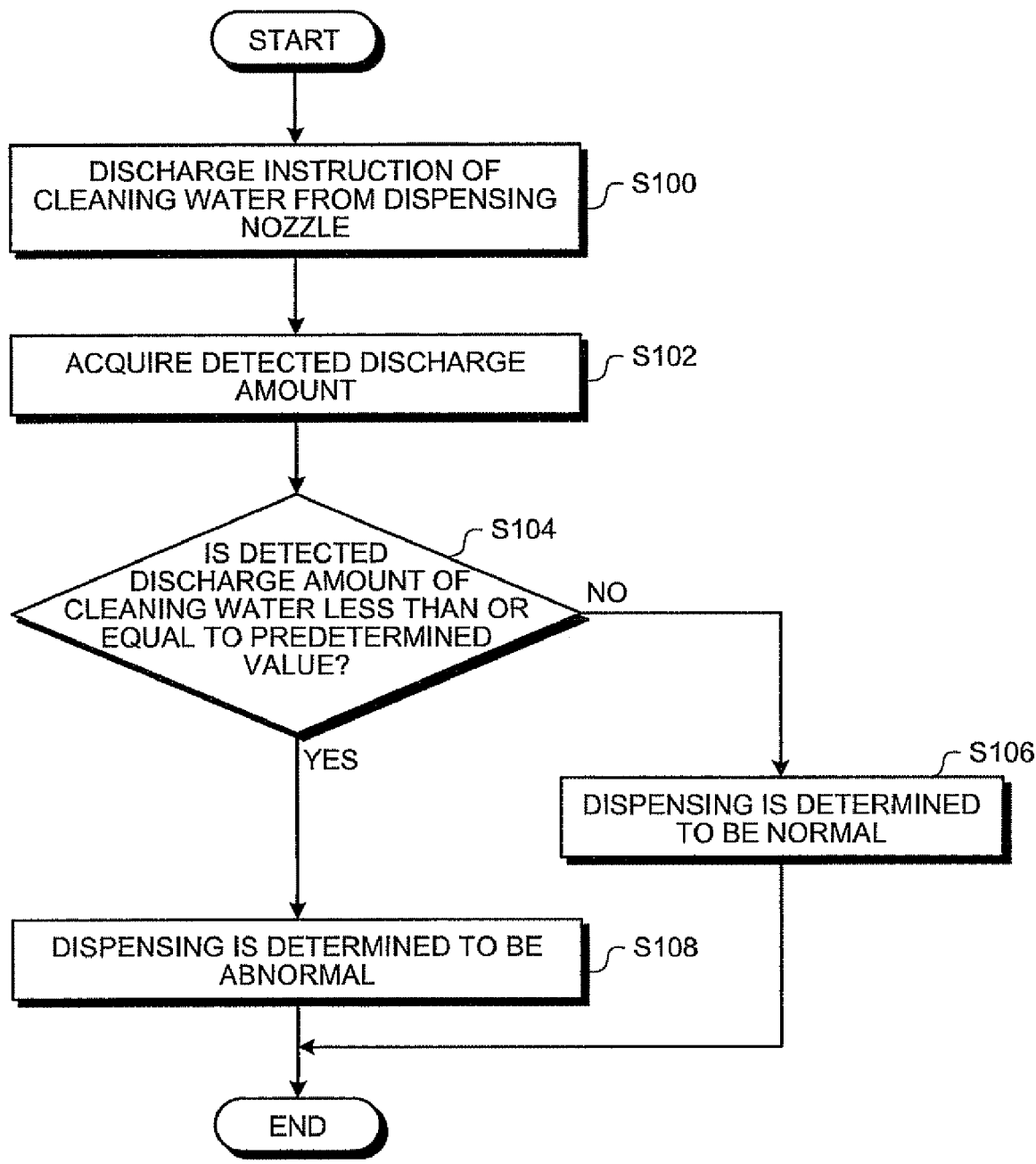
FIG. 5 is a flowchart of a determination procedure for an abnormality in dispensing in a specimen dispensing system.

Next, a determination procedure to determine whether there is the abnormality in dispensing in the specimen dispensing system 6 based on the discharge amount of the cleaning water discharged by the dispensing nozzle 6b is described with reference to the flowchart shown in FIG. 5. Firstly, the controller 10 follows an instruction input from the input unit 11 and instructs the dispensing nozzle 6b to discharge the cleaning water (Step S100). The instruction to discharge the cleaning water is carried out as the controller 10 outputs to the electromagnetic valve 68 a control signal to close the valve, and outputs to the pump drive unit 65 a control signal to drive the dispensing pump 64.

Next, the controller 10 acquires a detected discharge amount of the cleaning water 70 discharged into the cleaning tank 72 by the dispensing nozzle 6b that is detected by the sensors 74, 75 (Step S102).

Next, the controller 10 determines whether the detected discharge amount of the cleaning water is less than or equal to the predetermine value based on a discharge-amount signal input from the sensor 75 (Step S104). The determination is to determine whether the detected discharge amount of the cleaning water 70 detected by the sensors 74, 75 is over 90% of the pre-set discharge amount of the cleaning water 70. If the discharge amount of the cleaning water 70 is not less than or equal to the predetermined value, in other words, over 90% of the pre-set determined discharge amount (Step S104, No), the controller 10 determines that the dispensing is normal (Step S106), and terminates the determination operation.

On the other hand, the detected discharge amount of the cleaning water 70 is equal to or less than the predetermined value, in other words, equal to or less than 90% of the pre-set discharge amount (Step S104, Yes), the controller 10 determines that the dispensing is abnormal (Step S108), and notifies the same. The notification of the abnormality in dispensing is carried out as the controller 10 outputs a notification signal to the notifier 12, and displays the notification of the abnormality in dispensing on the display 12a or activates an alarm of an alerting device 12b. When the notification of the abnormality in dispensing is carried out, an operator carries out a cleaning of the pipe 61 or the dispensing nozzle 6b of the specimen dispensing system 6.

Figure 6:
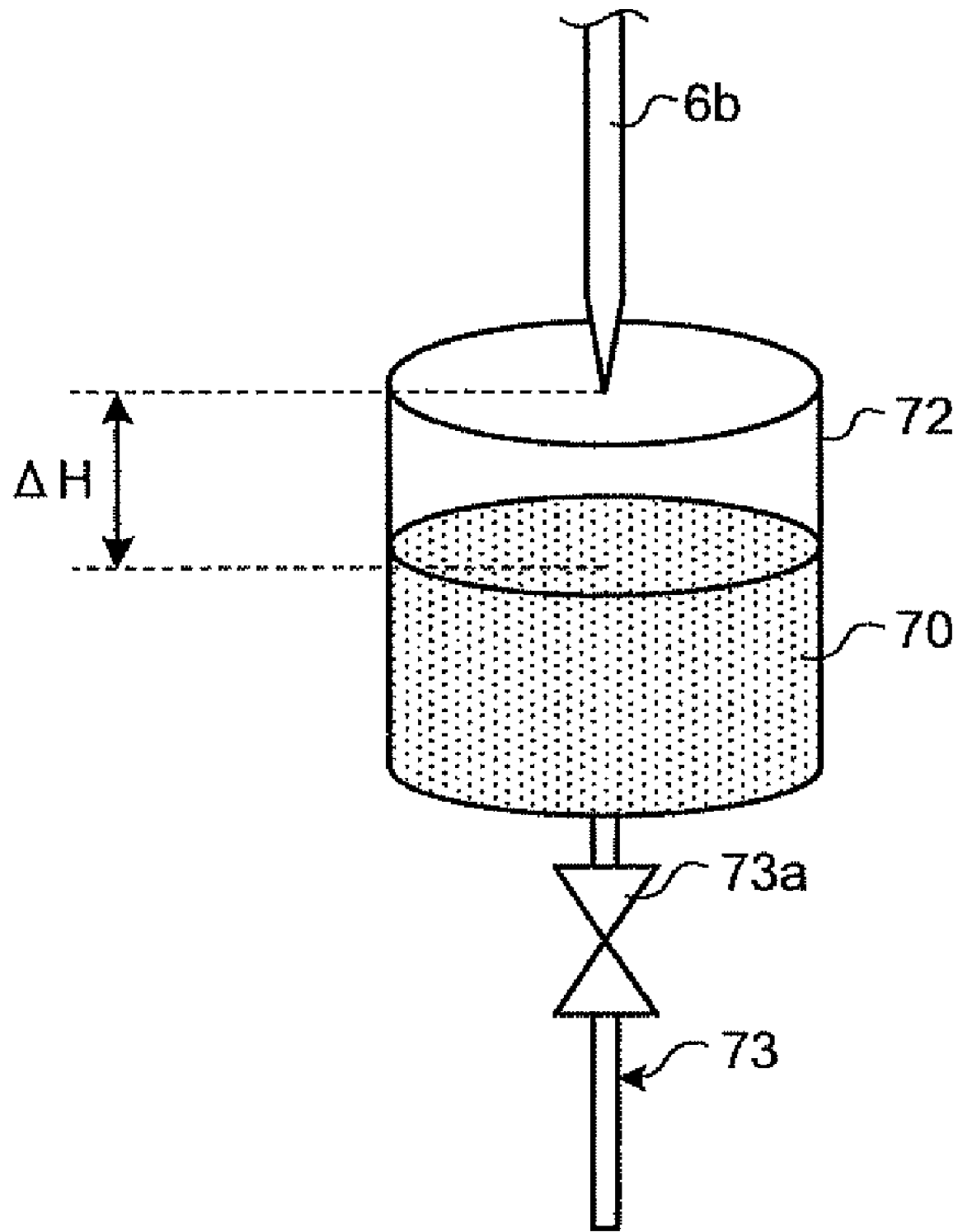
FIG. 6 is a perspective view of a cleaning tank and a dispensing nozzle according to a second embodiment of the present invention, to acquire the discharge amount of the cleaning water based on a downward amount of the dispensing nozzle.
Figure 7:
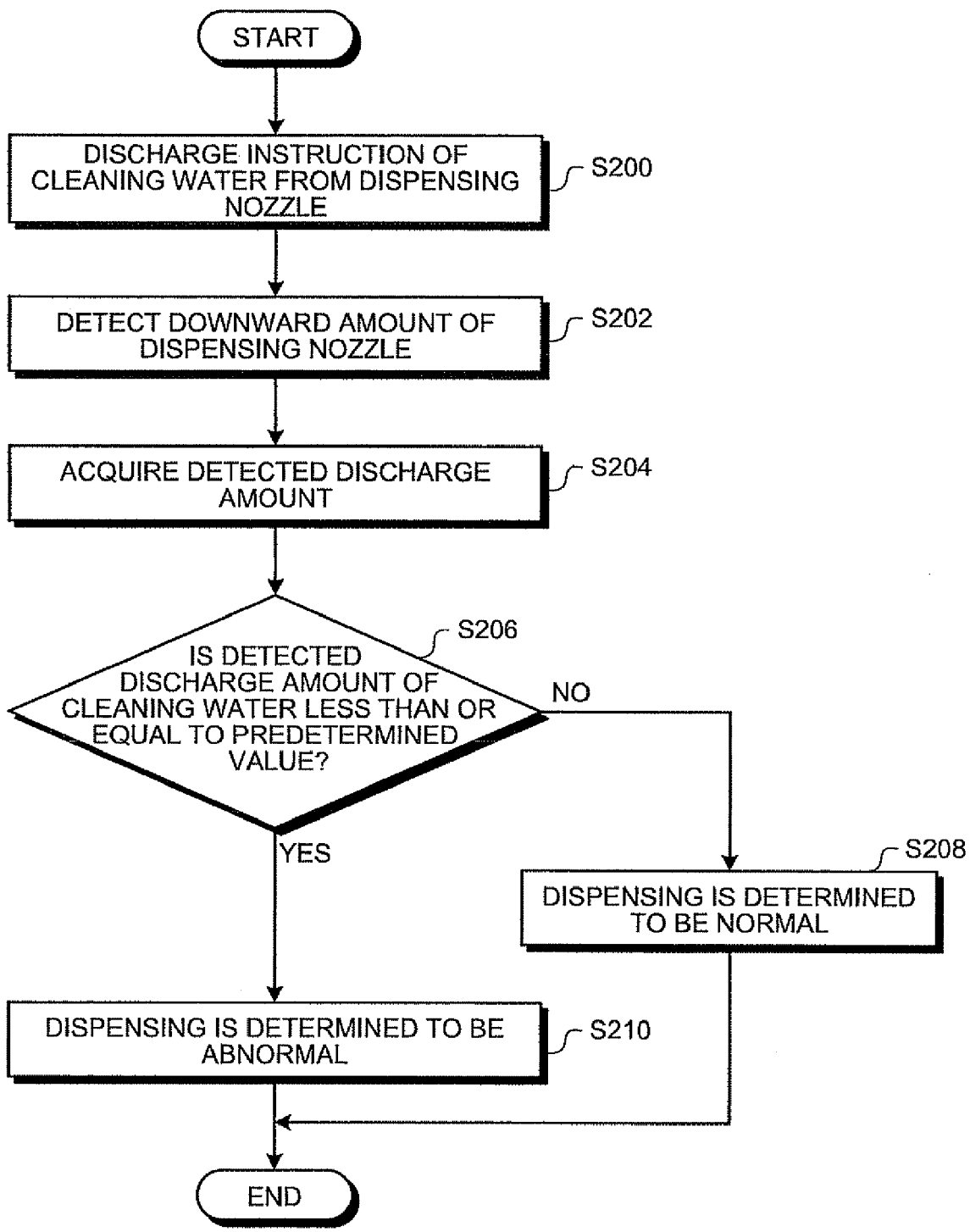
FIG. 7 is a flowchart for explaining a determination process for the abnormality in dispensing according to the second embodiment.

Next, a second embodiment according to an automatic analyzer and a method for determining an abnormality in dispensing of the dispensing system is described in detail with reference to the drawings. In the automatic analyzer and the method for determining an abnormality in dispensing of the dispensing system according to the first embodiment, the discharge amount of the cleaning water 70 is detected by the sensors 74, 75 attached to the cleaning tank 72. In the second embodiment, the discharge amount of the cleaning water 70 is acquired from a downward amount of the dispensing nozzle. FIG. 6 is a perspective view of a dispensing nozzle and a cleaning tank of the automatic analyzer. FIG. 7 is a flowchart to explain a determination procedure of the abnormality in dispensing according to the second embodiment.

As shown in FIG. 6, the discharge amount of the cleaning water discharged into the cleaning tank 72 by the dispensing nozzle 6b may be acquired from the downward amount ΔH, by which the dispensing nozzle 6b which is yet to dispense the cleaning water moves down to the cleaning water 70 after discharging the cleaning water. In this case, the nozzle drive unit 63 employs a stepping motor or the like which can accurately detect the downward movement ΔH (mm) of the dispensing nozzle 6b, and the dispensing nozzle 6b is connected to a liquid-surface detecting system which electrically detects a contact to a liquid surface of the cleaning water 70.

Further, the controller 10 detects the discharge amount of the cleaning water based on the downward amount ΔH (mm), which is detected from a control signal generated when the nozzle drive unit 63 moves down the dispensing nozzle 63b, and on a plane area (mm²) of an inside of the cleaning tank 72, which is previously acquired. Accordingly, the detected discharge amount of the detected cleaning water is compared with the pre-set discharge amount of the cleaning water 70 for the determination processor 10b to determine whether there is the abnormality in dispensing.

The description below is described based on the flowchart showing the determination procedure to determine whether there is the abnormality in dispensing in FIG. 7. Firstly, the controller 10 gives an instruction to the dispensing nozzle 6b to discharge the cleaning water following an instruction input from the input unit 11 (Step S200). The instruction to discharge the cleaning water is carried out as the controller 10 outputs to the electromagnetic valve 68 the control signal to close the valve, and outputs to the pump drive unit 65 the control signal to drive the dispensing pump 64.

Next, the controller 10 detects the downward amount of the dispensing nozzle 6b (Step S202). After that, the controller 10 acquires the detected discharge amount of the cleaning water from a variation amount of a liquid-surface position, which is difference between the detected downward amount of the dispensing nozzle 6b and the downward amount acquired last time, and from the plane area of the inside of the cleaning tank 72 (Step S204).

Next, the controller 10 determines whether the detected discharge amount of the cleaning water is over the predetermined value (Step S206). The determination is to determine whether the detected discharge amount of the cleaning water 70 detected by the controller 10 is over 90% of the pre-set discharge amount of the cleaning water 70. If the discharge amount of the cleaning water 70 is not less than or equal to the predetermined value, in other words, if the detected discharge amount is over 90% of the pre-set discharge amount (Step S206, No), the controller 10 determines that the dispensing is normal (Step S208), and terminates the determination operation.

On the other hand, if the detected discharge amount of the cleaning water 70 is equal to or less than 90% of the pre-set discharge amount (Step S206, Yes), the controller 10 determines that the dispensing is abnormal (Step S210), and notifies that there is the abnormality in dispensing similarly to the first embodiment.

Figure 8:
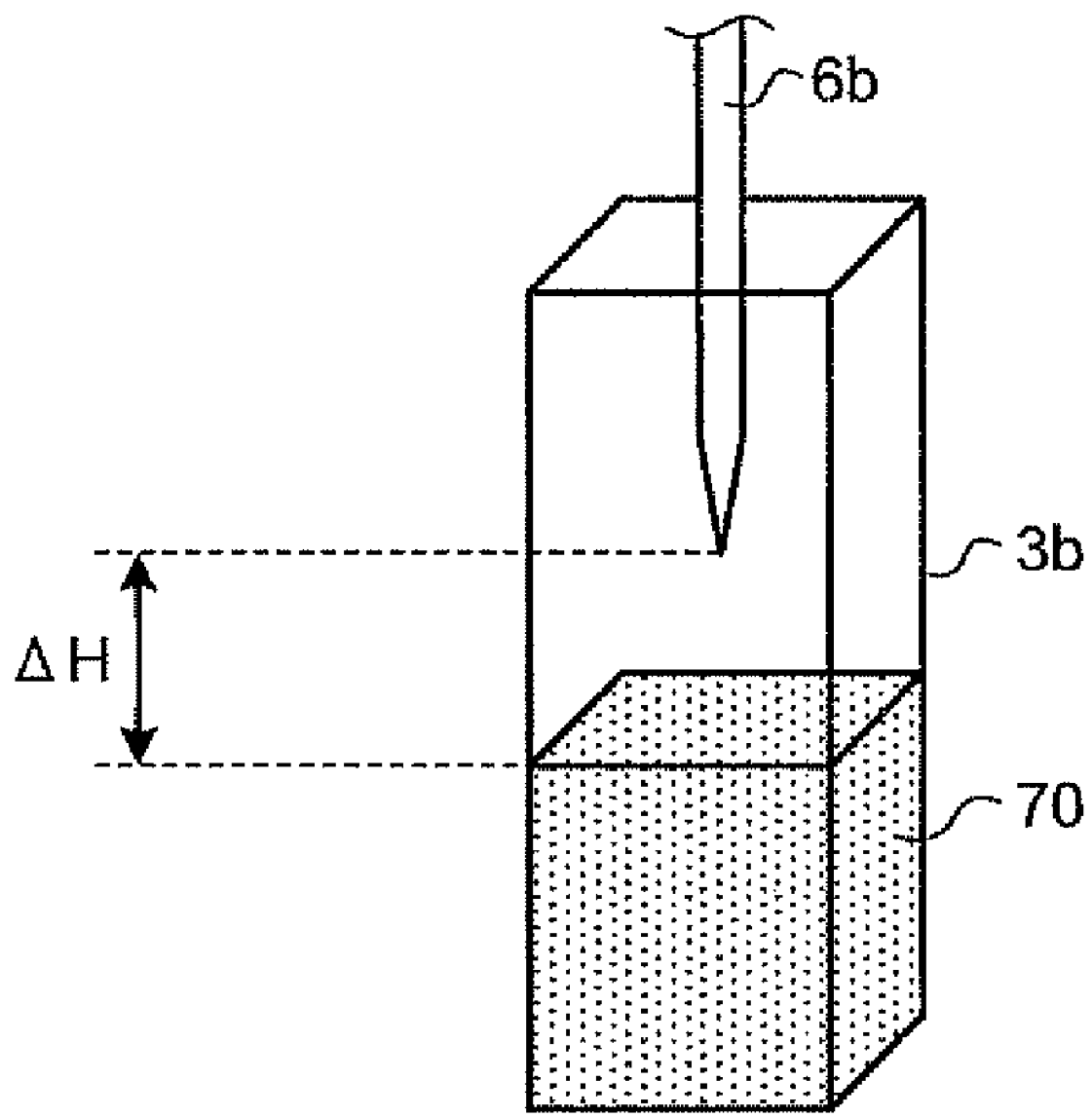
FIG. 8 is a perspective view of another embodiment acquiring the discharge amount of the cleaning water.

Further, as shown in FIG. 8, when the cleaning water is to be discharged into a reaction vessel such as a cuvette instead of the cleaning tank 72, the detected discharge amount may be acquired from a product of an inner plane area of a cuvette 3b and the downward amount ΔH, by which the dispensing nozzle 6b which is yet to dispense the cleaning water into a cuvette 3b moves down to the cleaning water 70 after discharging the cleaning water.

As described above, in the automatic analyzer and the method for determining an abnormality in dispensing of the dispensing system according to the present invention, the detected discharge amount of the cleaning water discharged by the dispensing nozzle 6b is compared with the pre-set discharge amount to determined whether there is an abnormality in dispensing.

Further, in the above-described embodiment, the automatic analyzer determines whether there is an abnormality in dispensing based on the discharge amount of the cleaning water in the specimen dispensing system 6. The automatic analyzer 1, however, can also determine whether there is an abnormality in dispensing based on the discharge amount of the cleaning water in the reagent dispensing system 7.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An automatic analyzer for analyzing a reaction liquid in which a specimen and a reagent have been reacted, comprising:
   a dispensing system that includes
      a dispensing nozzle by which the specimen and the reagent are dispensed; and
      a dispensing pipe connected to the dispensing nozzle and filled with a cleaning liquid, the dispensing nozzle being cleaned with the cleaning liquid discharged from the dispensing nozzle;
   a detector including two sensors that detects a discharge amount of the cleaning liquid discharged from the dispensing nozzle based on light signal emitted and received by the two sensors; and
   a determiner that determines whether the detected discharge amount of the cleaning liquid is over a predetermined value which is less than a pre-set discharge amount of the cleaning liquid, the determiner determining that the dispensing is abnormal if the detected discharge amount is equal to or less than the predetermined value.

2. The automatic analyzer according to claim 1, wherein the predetermined value is equal to or less than 90% of the pre-set discharge amount.

3. The automatic analyzer according to claim 1, further comprising
a notifier that notifies that the dispensing is abnormal by a display or an alert.

4. The automatic analyzer according to claim 1, wherein the detector further detects a decrease of the discharge amount of the cleaning liquid discharged from the dispensing nozzle thereby detecting variation of measurement data in advance.

5. A method for determining an abnormality in dispensing of a dispensing system in which a specimen and a reagent are dispensed by a dispensing nozzle connected to a dispensing pipe filled with a cleaning liquid, and the dispensing nozzle is cleaned with the cleaning liquid discharged from the dispensing nozzle, the method comprising:

detecting a discharge amount of the cleaning liquid discharged from the dispensing nozzle based on light signal emitted and received by two sensors; and determining whether the detected discharge amount of the cleaning liquid is over a predetermined value that is less than a pre-set discharge amount of the cleaning liquid, and determining that the dispensing is abnormal if the detected discharge amount is equal to or less than the predetermined value.

6. The method according to claim 5, further comprising detecting a decrease of the discharge amount of the cleaning liquid discharged from the dispensing nozzle thereby detecting variation of the measurement data in advance.

\* \* \* \* \*